US005855608A

United States Patent [19]
Brekke et al.

[11] Patent Number: 5,855,608
[45] Date of Patent: Jan. 5, 1999

[54] DEVICE AND METHODS FOR IN VIVO CULTURING OF DIVERSE TISSUE CELLS

[75] Inventors: John H. Brekke; Timothy Ringeisen, both of Duluth, Minn.

[73] Assignee: THM Biomedical, Inc., Duluth, Minn.

[21] Appl. No.: 367,510

[22] Filed: Dec. 30, 1994

Related U.S. Application Data

[63] Continuation-in-part of Ser. No. 242,557, May 13, 1994.
[51] Int. Cl.$^6$ ................................ A61F 2/02; A61K 9/14
[52] U.S. Cl. ................................ 623/11; 623/16; 424/487
[58] Field of Search .................................. 623/1, 11, 12, 623/16–20, 66, 901; 424/487

[56] References Cited

U.S. PATENT DOCUMENTS

| | | |
|---|---|---|
| 4,186,448 | 2/1980 | Brekke . |
| 4,642,120 | 2/1987 | Nevo et al. . |
| 5,041,138 | 8/1991 | Vacanti et al. . |
| 5,133,755 | 7/1992 | Brekke . |
| 5,152,791 | 10/1992 | Hakamatsuka et al. . |
| 5,294,446 | 3/1994 | Schlameus et al. . |
| 5,366,508 | 11/1994 | Brekke . |

FOREIGN PATENT DOCUMENTS

| | | |
|---|---|---|
| 0369034 | 5/1990 | European Pat. Off. . |
| 0505634 | 9/1992 | European Pat. Off. . |
| 2175506 | 12/1986 | United Kingdom . |
| WO9315694 | 8/1993 | WIPO . |
| WO9409722 | 5/1994 | WIPO . |

OTHER PUBLICATIONS

Synthesis and turnover of proteoglycans by human and bovine adult articular chondrocytes cultured in alginate beads, by H.J. Hauselmann, M.B. Aydelotte, B.L. Schumacher, K.E. Kuettner, S.H. Gitelis, and E.J.–M.A. Thonar, Matrix, 12, pp. 116–129, (1992).

Towards a synthetic articular cartilage, by P.H. Corkhill, J.H. Fitton, and B.J. Tighe, J. Biomater. Sci. Polymer Edn., 4 (6), pp. 615–630, (1993).

Neocartilage formation in vitro and in vivo using cells cultured on synthetic biodegradable polymers, by L.E. Freed, J.C. Marquis, A. Nohria, J. Emmanual, A.G. Mikos, and R. Langer, J. Biomed. Mat. Res., 27, pp. 11–23, (1993).

(List continued on next page.)

*Primary Examiner*—Robert A. Clarke
*Attorney, Agent, or Firm*—Peterson, Wicks, Nemer & Kamrath, P.A.

[57] ABSTRACT

An anatomically specific, bioresorbable, implant device for facilitating the healing of voids in bone, cartilage and soft tissue is disclosed. A preferred embodiment of using the implant device for facilitating the healing of a human joint lesion includes a cartilage region invested with an alginate microstructure joined with a subchondral bone region invested with a hyaluronan microstructure. The alginate selectively dispersed in the cartilage region enhances the environment for chondrocytes to grow articular cartilage. The hyaluronan selectively dispersed in the subchondral bone region enhances the environment for mesenchymal cells which migrate into that region's macrostructure and which differentiate into osteoblasts. The microstructures can be invested at varying concentrations in the regions. A hydrophobic barrier, strategically positioned within the subchondral bone region macrostructure, shields the chondrocytes from the oxygenated blood in subchondral cancellous bone. In the preferred form, the cartilage region includes a tangential zone including a network of intercommunicating void spaces having a horizontal orientation and in communication with synovial fluid and includes a radial zone including multiple void spaces oriented in both horizontal and vertical planes and providing intercommunication between the tangential zone and the subchondral bone region.

31 Claims, 7 Drawing Sheets

OTHER PUBLICATIONS

Porous polymer implants for repair of full–thickness defects of articular cartilage: an experimental study in rabbit and dog, by J. Klompmaker, H.W.B. Jansen, R.P.H. Veth, H.K.L. Nielsen, J.H. de Groot, and A.J. Pennings, Biomat., 13 (9), pp. 625–634, (1992).

Laminated three–dimensional biodegradable foams for use in tissue engineering, by A.G. Mikos, G. Sarakinos, S.M. Leite, J.P. Vacanti, and R. Langer, Biomat., 14 (5), pp. 323–330, (1993).

Preparation of poly(glycolic acid) bonded fiber structures for cell attachment and transplantation, by A.G. Mikos, Y. Bao, L.G. Cima, D.E. Ingber, J.P. Vacanti, and R. Langer, J. Biomed. Mat. Res., 27, pp. 183–189, (1993).

Effect of freeze–dried poly–L–lactic acid discs mixed with bone morphogenetic protein on the healing of rat skull defects by T. Miki, K. Harada, Y. Imai, and S. Enomoto, J. Oral Maxillofac. Surg., 52, pp. 387–391, (1994).

Attachment and survival of perichondrocytes in a porous polylactic acid (PLA) matrix: an in vitro study, by C.R. Chu, A.Z. Monosov, R.D. Coutts, and D. Amiel, Thirteenth Southern Biomedical Engineering Conference, Apr. 16–17, 1994, University of the District of Columbia, Washington, D.C.

Identification of hyaluronic acid binding sites in the extracellular domain of CD44, by R.J. Peach, D. Hollenbaugh, I. Stamenkovic, and A. Aruffo, J. Cell Bio., 122 (1), pp. 257–264 (Jul. 1993).

Hyaluronate can function as a cell adhesion molecule and CD44 participates in hyaluronate recognition, by K. Miyake, C.B. Underhill, J. Lesley, and P.W. Kincade, J. Exp. Med., 172, pp. 69–75, (1990).

Expression and modulation of CD44 variant isoforms in humans, by C.R. Mackay, H–J. Terpe, R. Stauder, W.L. Marston, H. Stark and U. Günthert, J. Cell Bio., 124 (1&2), pp. 71–82, (Jan. 1994).

Culture and differentiation of chondrocytes entrapped in alginate gels, by M. Grandolfo, P. D'Andrea, S. Paoletti, M. Martina, G. Silvestrini, E. Bonucci, and F. Vittur, Calcif. Tissue Int., 52, pp. 42–48, (1993).

Influence of matricial molecules on growth and differentiation of entrapped chondrocytes, by H. Ramdi, C. Legar, and M. Lievremont, Experi. Cell Res., 207, pp. 449–454, (1993).

Rabbit articular chondrocytes in alginate gel: characterisation of immobilized preparations and potential applications, by C. Tamponnet, H. Ramdi, J–B. Guyot, and M. Lievremont, Appl. Microbiol. Biotechnol., 37, pp. 311–315, (1992).

DEVICE AND METHODS FOR IN VIVO CULTURING OF DIVERSE TISSUE CELLS

CROSS REFERENCE

This application is a continuation-in-part of U.S. Ser. No. 08/242,557 filed May 13, 1994.

BACKGROUND

1. Field of the Invention

The present invention generally relates to the transport and culturing of cells. Specifically, in one aspect, the present invention employs an anatomically specific device for regenerating at least first and second, juxtaposed tissues having different histologic patterns, which includes a first region having an internal three-dimensional architecture to approximate the histological pattern of the first tissue and a second region having an internal three-dimensional architecture to approximate the histologic pattern of the second tissue. In addition, the present invention relates to a domain for the trapping and controlled growth of cells as such functions relate to tissue regeneration. In particular, a permeable bioresorbable polymer assembly is designed in such a way as to allow tissue integration of the assembly while delaying, limiting or preventing total penetration through the device by tissue cells. Such an assembly can be used to: 1) provide space maintenance and regeneration of lost tissue external to the unit; and/or 2) control growth of tissue forming cells within the unit.

2. Statement of Related Art

The medical repair of bones and joints in the human body presents significant difficulties, in part due to the materials involved. Each bone has a hard, compact exterior surrounding a spongy, less dense interior. The long bones of the arms and legs, the thigh bone or femur, have an interior containing bone marrow. The material bones are composed of mainly is calcium, phosphorus, and the connective tissue substance known as collagen.

Bones meet at joints of several different types. Movement of joints is enhanced by the smooth hyaline cartilage that covers the bone ends and by the synovial membrane that lines and lubricates the joint. For example, consider a cross-section through a hip joint. The head of the femur is covered by hyaline cartilage. Adjacent to that cartilage is the articular cavity. Above the articular cavity is the hyaline cartilage of the acetabulum which is attached to the ilium. The ilium is the expansive superior portion of the hip bone.

Cartilage damage produced by disease such as arthritis or trauma is a major cause of physical deformity and dehabilitation. In medicine today, the primary therapy for loss of cartilage is replacement with a prosthetic material, such as silicon for cosmetic repairs, or metal alloys for joint realignment. The use of a prosthesis is commonly associated with the significant loss of underlying tissue and bone without recovery of the full function allowed by the original cartilage. The prosthesis is also a foreign body which may become an irritating presence in the tissues. Other long-term problems associated with the permanent foreign body can include infection, erosion and instability.

The lack of a truly compatible, functional prosthesis subjects individuals who have lost noses or ears due to burns or trauma to additional surgery involving carving a piece of cartilage out of a piece of lower rib to approximate the necessary contours and insert the cartilage piece into a pocket of skin in the area where the nose or ear is missing.

In the past, bone has been replaced using actual segments of sterilized bone or bone powder or porous surgical steel seeded with bone cells which were then implanted. In most cases, repair to injuries was made surgically. Patients suffering from degeneration of cartilage had only pain killers and anti-inflammatories for relief.

Until recently, the growth of new cartilage from either transplantation or autologous or allogeneic cartilage has been largely unsuccessful. Consider the example of a lesion extending through the cartilage into the bone within the hip joint. Picture the lesion in the shape of a triangle with its base running parallel to the articular cavity, extending entirely through the hyaline cartilage of the head of the femur, and ending at the apex of the lesion, a full inch (2.54 cm) into the head of the femur bone. Presently, there is a need to successfully insert an implant device consisting of a macrostructure and a microstructure for containing and transporting cartilage cells and bone cells together with supporting nutrients, growth factors and morphogens, which will assure survival and proper future differentiation of these cells after transplantation into the recipient tissue defect. Presently, cartilage cells, called chondrocytes, when implanted along with bone cells, can degenerate into more bone cells because hyaline cartilage is an avascular tissue and must be protected from intimate contact with sources of high oxygen tension such as blood. Bone cells, in contrast, require high oxygen levels and blood.

Most recently, two different approaches to treating articular lesions have been advanced. One approach such as disclosed in U.S. Pat. No. 5,041,138 is coating bioderesorbable polymer fibers of a structure with chemotactic ground substances. No detached microstructure is used. The other approach such as disclosed in U.S. Pat. No. 5,133,755 uses chemotactic ground substances as a microstructure located in voids of a macrostructure and carried by and separate from the biodegradable polymer forming the macrostructure. Thus, the final spatial relationship of these chemotactic ground substances with respect to the bioresorbable polymeric structure is very different in U.S. Pat. No. 5,041,138 from that taught in U.S. Pat. No. 5,133,755.

The fundamental distinction between these two approaches presents three different design and engineering consequences. First, the relationship of the chemotactic ground substance with the bioresorbable polymeric structure differs between the two approaches. Second, the location of biologic modifiers carried by the device with respect to the device's constituent materials differs. Third, the initial location of the parenchymal cells differs.

Both approaches employ a bioresorbable polymeric structure and use chemotactic ground substances. However, three differences between the two approaches are as follows.

I. Relationship of Chemotactic Ground Substances with the Bioresorbable Polymeric Structure.

The design and engineering consequence of coating the polymer fibers with a chemotactic ground substance is that both materials become fused together to form a single unit from structural and spatial points of view. The spaces between the fibers of the polymer structure remain devoid of any material until after the cell culture substances are added.

In contrast, the microstructure approach uses chemotactic ground substances as well as other materials, separate and distinct from the bioresorbable polymeric macrostructure. The microstructure resides within the void spaces of the macrostructure and only occasionally juxtaposes the macrostructure. Additionally, the microstructure approach uses polysaccharides and chemotactic ground substances spacially separate from the macrostructure polymer and forms an identifiable microstructure, separate and distinct from the macrostructure polymer.

The design and engineering advantage to having a separate and distinct microstructure capable of carrying other biological active agents can be appreciated in the medical treatment of articular cartilage. RGD attachment moiety of fibronectin is a desirable substance for attaching chondrocytes cells to the lesion. However, RGD attachment moiety of fibronectin is not, by itself, capable of forming a microstructure of velour in the microstructure approach. Instead, RGD is blended with a microstructure material prior to investment within macrostructure interstices and is ultimately carried by the microstructure velour.

II. Location of Biologic Modifiers Carried by a Device with Respect to the Device's Constituent Materials.

Coating only the polymer structure with chemotactic ground substances necessarily means that the location of the chemotactic ground substance is only found on the bioresorbable polymeric structure fibers. The microstructure approach uses the microstructure to carry biologic modifiers such as growth factors, morphogens, drugs, etc. The coating approach can only carry biologic modifiers with the biodegradable polymeric structure.

III. Initial Location of the Parenchymal Cell.

Because the coating approach attaches the chemotactic ground substances to the surfaces of the structure polymer and has no microstructure resident in the void volume of the device, the coating approach precludes the possibility of establishing a network of extracellular matrix material, specifically a microstructure, within the spaces between the fibers of the polymer structure once the device is fully saturated with cell culture medium. The coating approach predetermines that any cells introduced via culture medium will be immediately attracted to the surface of the structure polymer and attach thereto by virtue of the chemotactic ground substances on the polymer's surfaces.

The consequence of confining chemotactic ground substances to only the surfaces of the polymeric structure places severe restrictions on the number of cells that can be accommodated by the coated device. These restrictions on cell capacity are enforced by two limiting factors:

1) a severely limited quantity of chemotactic ground substance that can be incorporated within the device; and 2) a surface area available for cell attachment that is limited by the surface area supplied by the structure polymer.

In contrast to the coating approach, the microstructure approach, by locating chemotactic ground substances in the void spaces of the device, makes available the entire void volume of the device to accommodate their chemotactic ground substance microstructure.

In so far as it relates to a biologic cell trap for controlled growth and guided tissue regeneration, recent years have increased knowledge concerning biological mechanisms involved in the restoration of periodontal defects which has led to a method of treatment known as Guided Tissue Regeneration. This concept is based on the theory of space maintenance for the periodontal bone defect under treatment. Soft tissue is removed from the defect and a barrier is placed between the surrounding soft tissue and the periodontal defect (void) in alveolar bone. The barrier prevents soft tissue from returning to the defect (void) while allowing the slower growing bone sufficient time to fill the void and reestablish attachment with the tooth. These barriers can be broken down into two major groups: 1) Bioresorbable/Bioerodable; and 2) Non-Bioresorbable/Bioerodable. Those barriers which are not bioresorbable (polytetrafluorethylene, titanium, etc.) must be removed by a second surgery resulting in additional surgical trauma and risk of damage to newly regenerated bone by compromise of its collateral circulation. Those barriers which are bioresorbable have one of two drawbacks. They are either solid, in which case they prevent interstitial fluid exchange, or they are permeable and allow rapid penetration of soft tissue through the device. Thus, a unique design is needed in order to limit or prevent tissue penetration while still allowing for free exchange of interstitial fluid.

U.S. Pat. Nos. 4,181,983 and 4,186,444 define porous bioresorbable polymer devices. These devices, designed to treat tissue deficiencies, are comprised of a bioresorbable polymer fabricated in architecture resembling cancellous bone, allowing for rapid and complete penetration of soft and hard tissue through the devices. U.S. Pat. No. 3,902,497 meets the general description of U.S. Pat. Nos. 4,181,983 and 4,186,444 and will also allow complete soft tissue penetration in a short period of time.

U.S. Pat. No. 4,442,655 teaches a fibrin matrix formed in an aqueous solution which, once placed in mammalian tissue,. will collapse and afford no barrier function to soft tissue invasion.

U.S. Pat. Nos. 4,563,489; 4,596,574; and 4,609,551, although different from U.S. Pat. Nos. 4,181,483 and 4,186,444, are designed to accomplish the same goal; repair tissue deficiencies and create a continuous, uninterrupted mend. This is also the goal of U.S. Pat. No. 5,041,138, in which the device is composed of branching bioresorbable sutures.

None of the aforementioned devices, however, is designed to operate as a cell trap or barrier. Each encourages rapid ingrowth of tissue which will escape the device and invade the defect void.

SUMMARY AND DETAILED DESCRIPTION OF THE INVENTION

The anatomically specific device is a living prosthesis or implant for transport and for in vivo culturing of tissue cells in a diverse tissue lesion. The entire macrostructure of this device is composed of a bioresorbable polymer.

The anatomically specific device integrates a macrostructure, microstructure, free precursor cells cultured in vitro or from tissue, and biologically active agents, such as associated growth factors, morphogens, drugs and therapeutic agents.

The anatomically specific device in the embodiment designed for treating a cartilage and bone lesion has two main regions: a cartilage region and a subchondral bone region.

The cartilage region has a macrostructure composed of two distinct zones. The tangential zone of the cartilage region has intimate contact with synovial fluid. The radial zone located between the tangential zone and the subchondral bone region and comprising about 70% to 90% of the cartilage region is distinguished by vertically oriented plates which are fenestrated by multiple voids. The radial zone of the cartilage region is intimately bound to the macrostructure of the subchondral region at an interface surface.

The microstructure material of the cartilage region in the most preferred form is alginate or hyaluronan. Alginate, also known as alginic acid, is used for the transport of both in vitro and in vivo cultured cells and the establishment of an in vivo cell culture system within the device. Alginic acid, though having no chemotactic properties, is especially suitable for use in a device for treating articular cartilage defects because it facilitates the culturing and transport of chondrocytes.

The structure and the strategic location of the alginate microstructure inside the macrostructure provides the opportunity to segregate microstructure material from the subchondral bone region. The alginate microstructure has a primary function of delivering chondrocytes only to the cartilage region of the device by sequestering the chondrocyte cell population with the in vitro cell culture medium in its alginate gel. The microstructure has a secondary function of presenting enough chondrocytes to the subchondral bone region immediately adjacent to the cartilage regions to establish a competent osteo-chondral bond.

The selective concentration gradient of microstructure material may be selectively varied within certain regions of the macrostructure void to affect different biologic characteristics critical to different tissue requirements.

The microstructure of a single device may be composed of multiple different materials, some without chemotactic properties, in different regions of macrostructure void space depending upon varying tissue and biologic characteristics and requirements.

The subchondral bone region of the anatomically specific device includes a macrostructure composed of a biologically acceptable, bioresorbable polymer arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448). Polylactic acid (PLA), fabricated in the 3-D architecture of intercommunicationg voids described above is the polymer currently used to form the macrostructure. Other members of the hydroxy acid group of compounds can also be used as can any bioresorbable polymer if fabricated into a similar architecture.

The gross, or macro, structure of the invention fulfills three major functions for chondrogenesis and osteogenesis: 1) restoration of mechanical architectural and structural competence; 2) provides biologically acceptable and mechanically stable surface structure suitable for genesis, growth and development of new non-calcified and calcified tissue; and 3) functions as a carrier for other constituents of the invention which do not have mechanical and structural competence.

The microstructure of the implant device is composed of various polysaccharides which, in a preferred form, is alginate but can also be hyaluronic acid (abbreviated by HY). Intersties of the polylactic acid macrostructure of the body member are invested with the microstructure substance in the form of a velour having the same architecture of interconnecting voids as described for the macrostructure, but on a microscopic scale. Functions of the chemotactic ground substance microstructure (i.e. HY) are listed as: 1) attraction of fluid blood throughout the device; 2) chemotaxis for mesenchymal cell migration and aggregation; 3) carrier for osteoinductive and chondro-inductive agent(s); 4) generation and maintenance of an electro-negative wound environment; and 5) agglutination of other connective tissue substances with each other and with itself. Other examples of chemotactic ground substances are fibronectin and, especially for the reconstruction of articular cartilage, an RGD attachment moiety of fibronectin.

The osteoinductive agent, bone morphogenetic protein, has the capacity to induce primitive mesenchymal cells to differentiate into bone forming cells. Another osteogenic agent, bone derived growth factor, stimulates activity of more mature mesenchymal cells to form new bone tissue.

Other biologically active agents which can be utilized, especially for the reconstruction of articular cartilage, include transforming growth factor B (beta) and basic fibroblastic growth factor.

In a further aspect of the present invention, the anatomically specific implant device acts as a transport device of precursor cells harvested for the production of connective tissue. The device with its secured precursor cells can be press fit into the site of lesion repair. In a preferred aspect of the present invention, the microstructure velour (i.e. hyaluronan or alginate in the most preferred form) treated with an RGD attachment moiety of fibronectin facilitates the attachment of free, precursor cells to be carried to the lesion repair site.

Significant advantages and features of the present invention include:

1. The arrangement of fenestrated polymer strands of the tangential region produces a network of intercommunicating void spaces which have a horizontal orientation with respect to void spaces of the radial zone, thus making this construction anatomically specific for articular cartilage tissue.
2. The cartilage region's radial zone provides void spaces in horizontal planes which penetrate the vertically orientated polymer sheets and create intercommunications between the vertically positioned void spaces.
3. The radial zone of the cartilage region at the interface surface with the subchondral bone region provides a honeycomb pattern of pores with an uninterrupted space communicating from the interface surface, through the radial and tangential zones, to the pores which ultimately accesses the synovial fluid.
4. The hydrophobic barrier creates a strategic zone without interrupting the continuity of the macrostructure polymer of the subchondral bone region and further without introducing any chemical change in the macrostructure polymer.
5. The microstructure is strategically located within one, or multiple, discrete locales of the macrostructure void network while other locales of the macrostructure void network remain devoid of microstructure material.
6. The concentration gradients of microstructure material are selectively varied within certain regions of macrostructure voids to affect different biologic characteristics critical to different tissue requirements.
7. A microstructure is provided to a single anatomically specific device having a composition of multiple different materials in different regions of macrostructure voids according to the varying tissue and biologic characteristic requirements.
8. The use of a microstructure within a macrostructure provides multiple locations for transport of one or more types of biologic modifier cargo:
    1) onto the surface of the macrostructure;
    2) entrapped between the macrostructure and the microstructure;
    3) onto the surface of the microstructure;
    4) inside the microstructure; and/or
    5) within the hydration domains of the microstructure and yet detached from the polysaccharide of the microstructure as well as detached from the polymer of the macrostructure.
9. The three-dimensional configuration of the cell is preserved.
10. The entire surface area of each cell is preserved in optimum condition for interaction with the microstructure and its cargo of biologically active agents.

11. Each cell is coated with microstructure material which, in the case of hyaluronic acid, is composed of a high percentage of naturally occurring extracellular matrix.
12. Free cells are maintained in a semi-fluid environment so that the cells can move to establish multiple regions of optimum cell density.
13. The cells are maintained in close proximity to high concentrations of free, solubilized and unattached biologically active agents.
14. A transport for biologically active agents is provided.
15. A transport for osteoinductive/osteogenic and/or chondroinductive/chondrogenic agents, as well as other therapeutic substances (i.e. living cells appropriate for the tissue under treatment, cell nutrient media, varieties of growth factors, morphogens and other biologically active proteins) are provided.
16. An electronegative environment is created which is conducive to osteogenesis/chondrogenesis.
17. The need for more surgery to remove the device is eliminated since it is bioresorbable in its entirety.
18. A transport for precursor repair cells to lesion repair sites is created.
19. The attachment of free, precursor cells to the device and to the repair site is facilitated.

Objects of the present invention include:
1. Joins bioresorbable polymers of different architectures and chemical profiles into a single unit whose composite architectures are specifically ordered to duplicate the arrangements of parenchymal cells and stromal tissue of the tissue or organ under treatment and whose constituent polymers are specifically synthesized to possess chemical profiles appropriate for their particular locations within the whole. This object of the invention is expressed in the example of a device for treatment of articular cartilage defects in the most preferred form. The cartilage region architecture is joined to the subchondral bone region (cancellous bone) architecture to form a bioresorbable polymer implant having an anatomically specific architecture for articular cartilage.
2. Strategically positions microstructure material in that specific portion of the complete device to perform the particular unique functions required by the particular tissues being treated.
3. Segregates microstructure material within the anatomically specific device according to the special biologic functions of a particular implant.
4. Delivers chondrocytes only to the cartilage region of the device and supports their life functions in the cartilage defect by sequestering the chondrocyte cell population together with the in vitro cell culture medium in its microstructure (alginate) gel.
5. Presents enough chondrocytes to the subchondral bone region immediately adjacent to the cartilage region so as to assure that a competent osteo-chondral bond is established between the newly developed cartilage and the newly developed bone.
6. Provides a bioresorbable structure to carry and to support cell attachment enhancing material such as a chemotactic ground substance which is in the form of a filamentous velour having incomplete, interconnecting intersticies.
7. Generates electronegative potentials by maintaining an alginate or HY-fluid phase and PLA structural phase interface, as well as by the electronegative chemical property of alginate or HY alone.
8. Creates biophysical conditions and environment such that exogenous electric signals can be applied to the implant device to produce a synergistic effect with the endogenous currents generated by alginate or HY/PLA surface interactions and the intrinsic electronegativity of the microstructure.
9. Provides a unique juxtaposition of polylactate, alginate/hyaluronic acid and chemical osteoinductive/osteogenic and/or chondroinductive/chondrogenic agents.
10. Juxtaposes cell attachment enhancing material such as a chemotactic ground substance with a biodegradable polymer of either solid, open cell meshwork form, or in either form or both forms.
11. Provides a biodegradable structure to transport and to support precursor repair cells for repair sites.
12. Creates conditions and environments for facilitating the attachment of free, precursor cells for carriage to the repair site.

DESCRIPTION OF THE PREFERRED ANATOMICALLY SPECIFIC DEVICE EMBODIMENT

Figure 1:
FIG. 1 is a top view of the macrostructure and architecture of the tangential zone of the cartilage region with no microstructure alginate shown.
Figure 2:
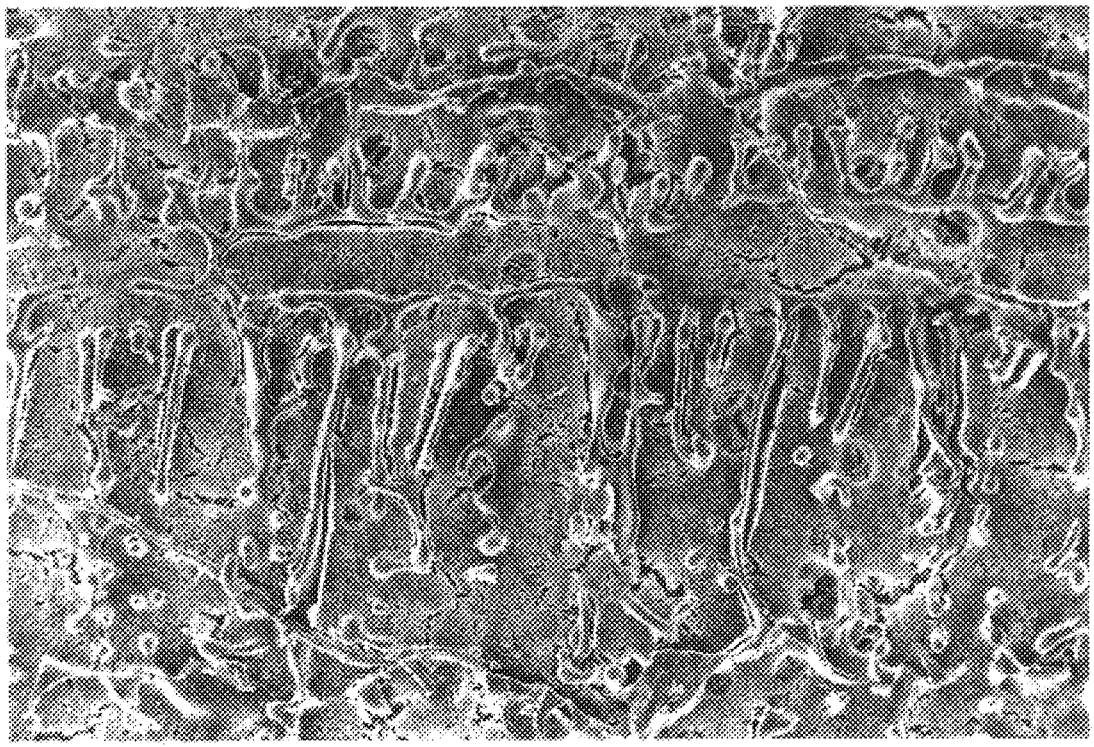
FIG. 2 is a top view of a cartilage region of a tangential zone as in FIG. 1 invested with alginate microstructure.
Figure 3:
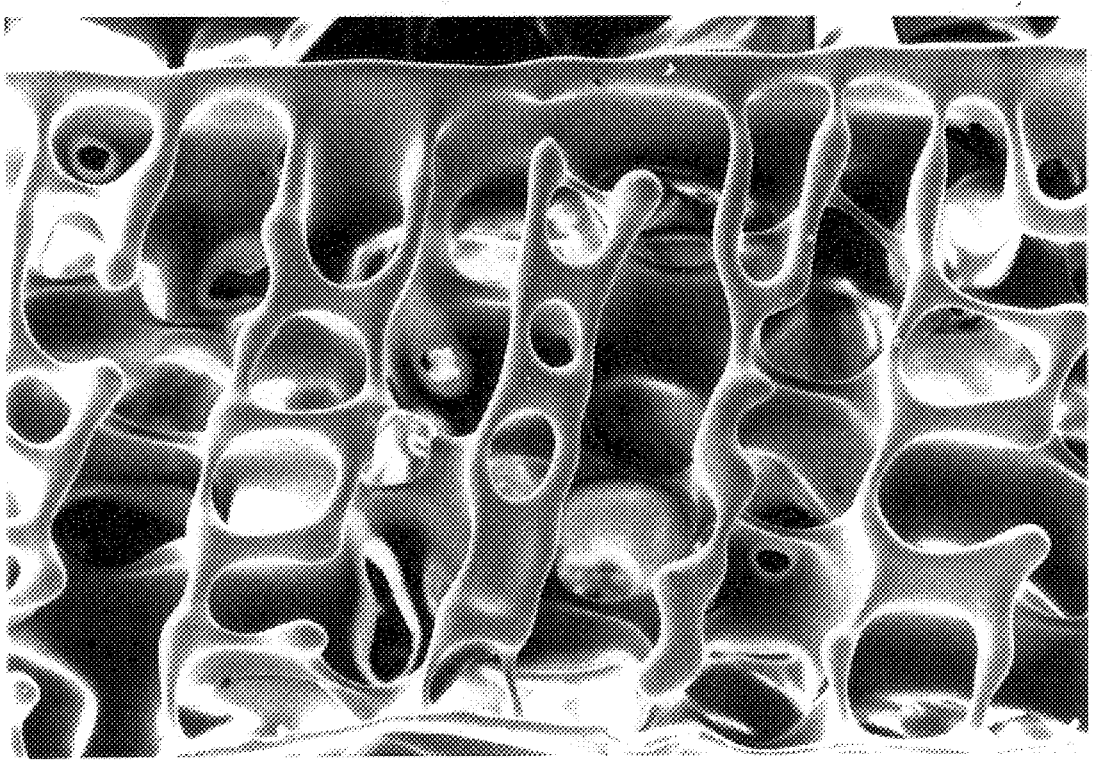
FIG. 3 is an enlarged view of FIG. 1.
Figure 4:
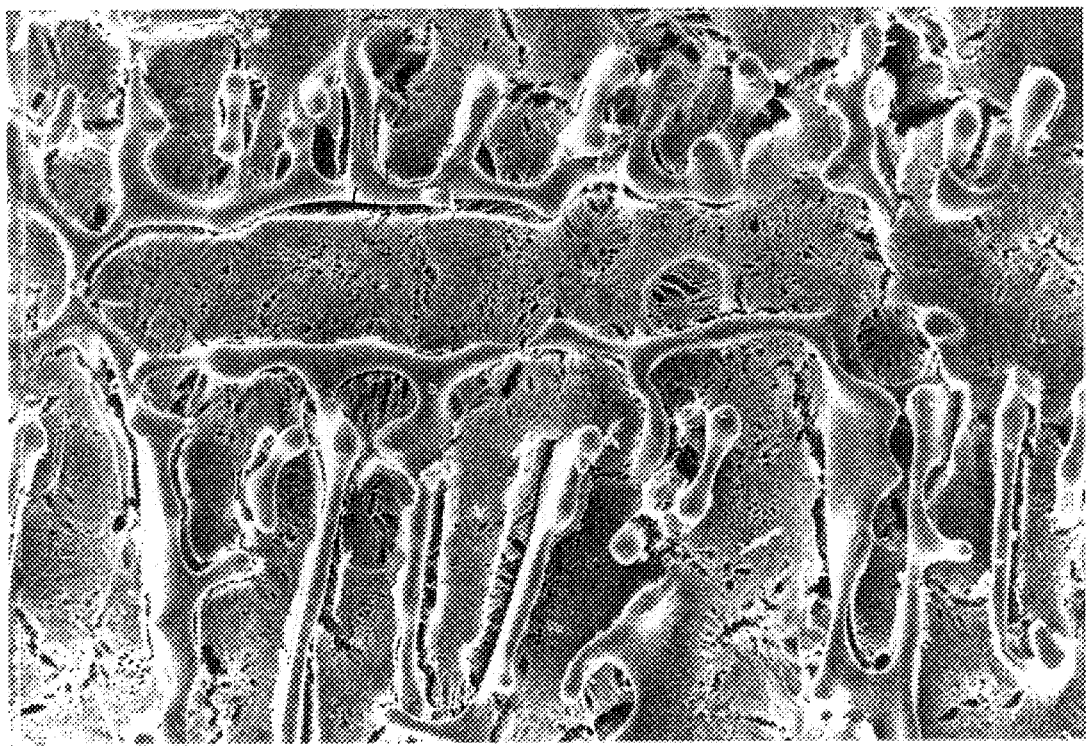
FIG. 4 is an enlarged view of FIG. 2.
Figure 5:
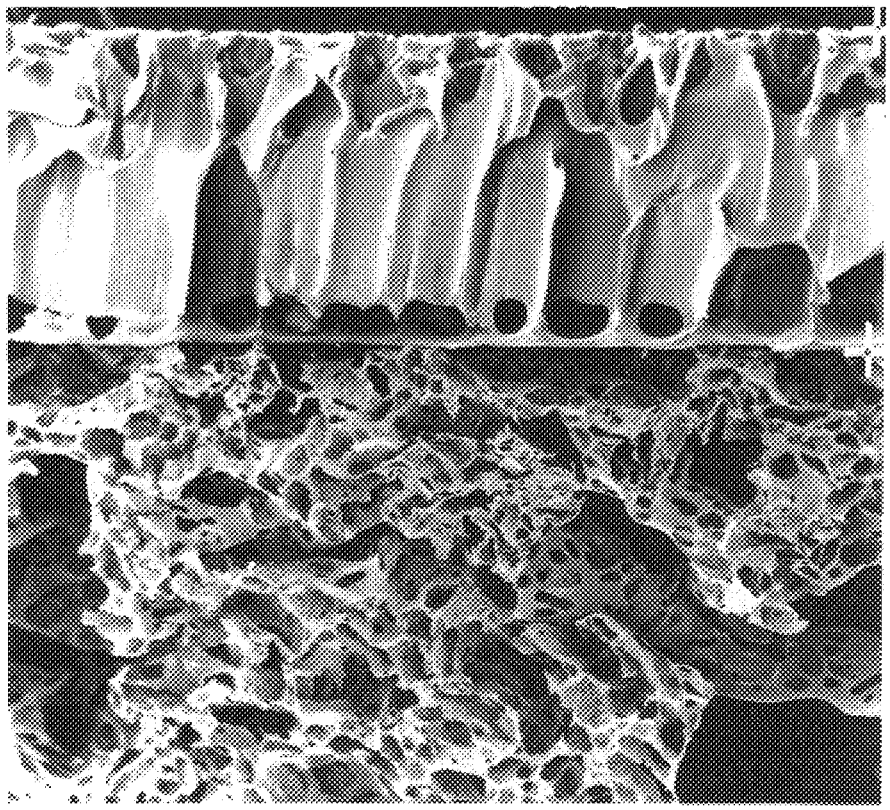
FIG. 5 is a cross-sectional view through the entire device without any microstructure.
Figure 6:
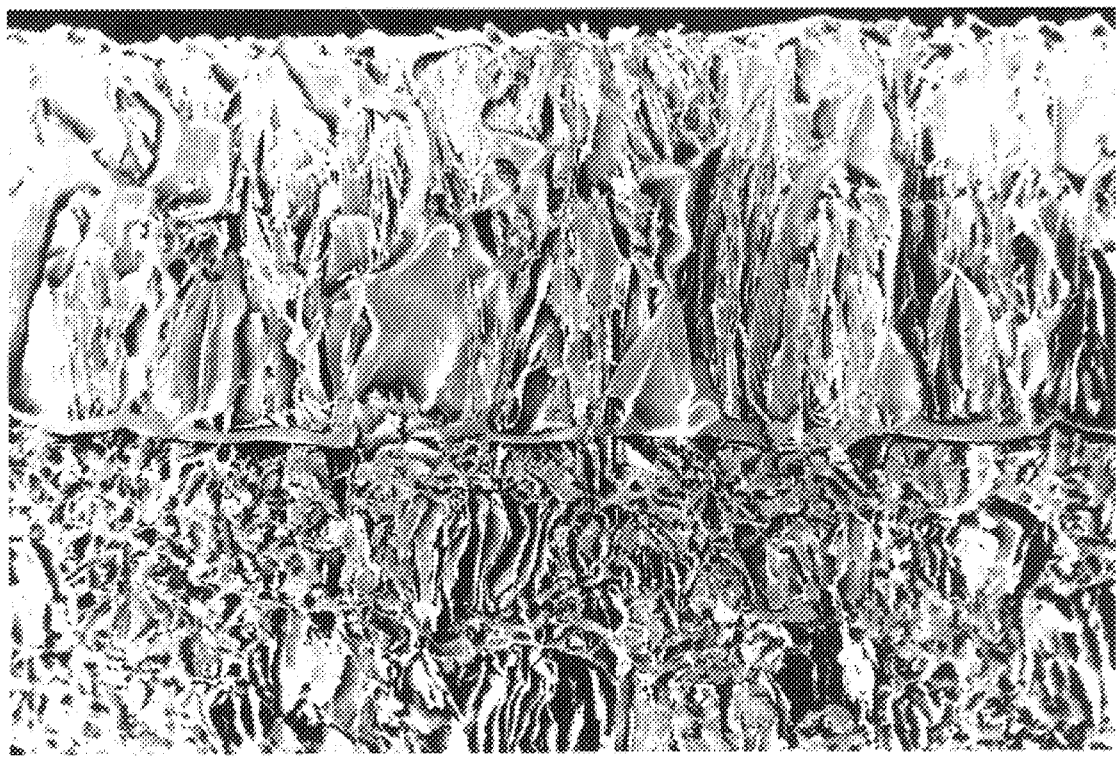
FIG. 6 is a cross-sectional view through the entire device invested with alginate microstructure.
Figure 7:
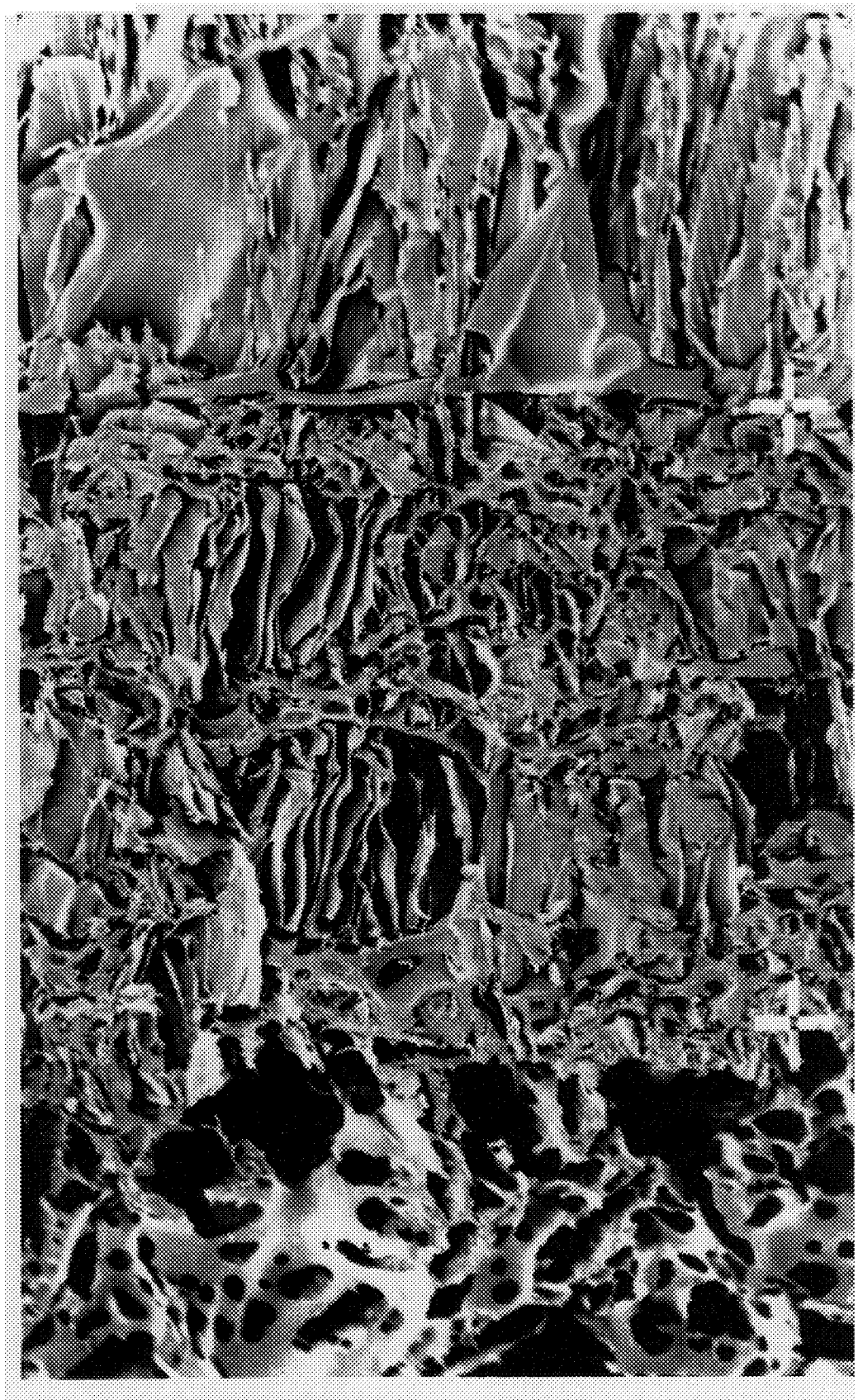
FIG. 7 is a cross-sectional view through the entire device showing a hydrophobic barrier.
Figure 8:
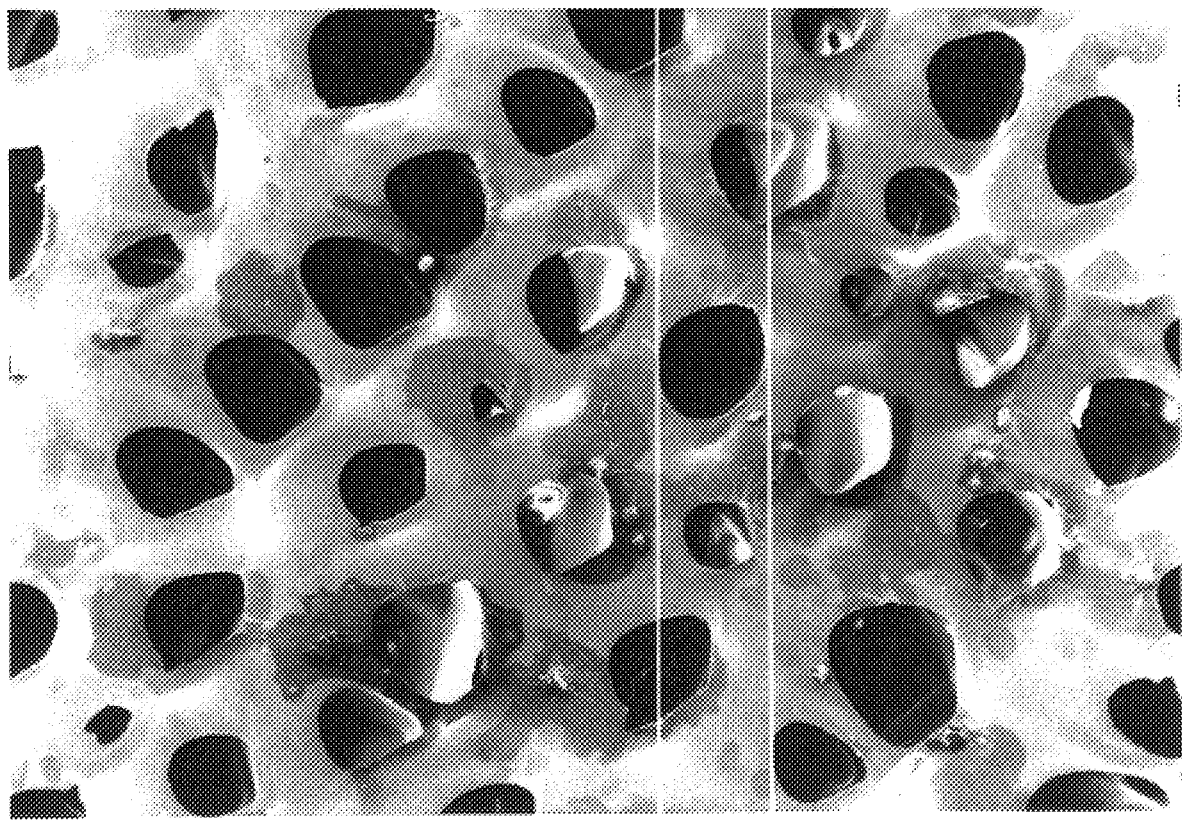
FIG. 8 is a cross-sectional view of the radial zone of the cartilage region at the interface surface.
Figure 9:
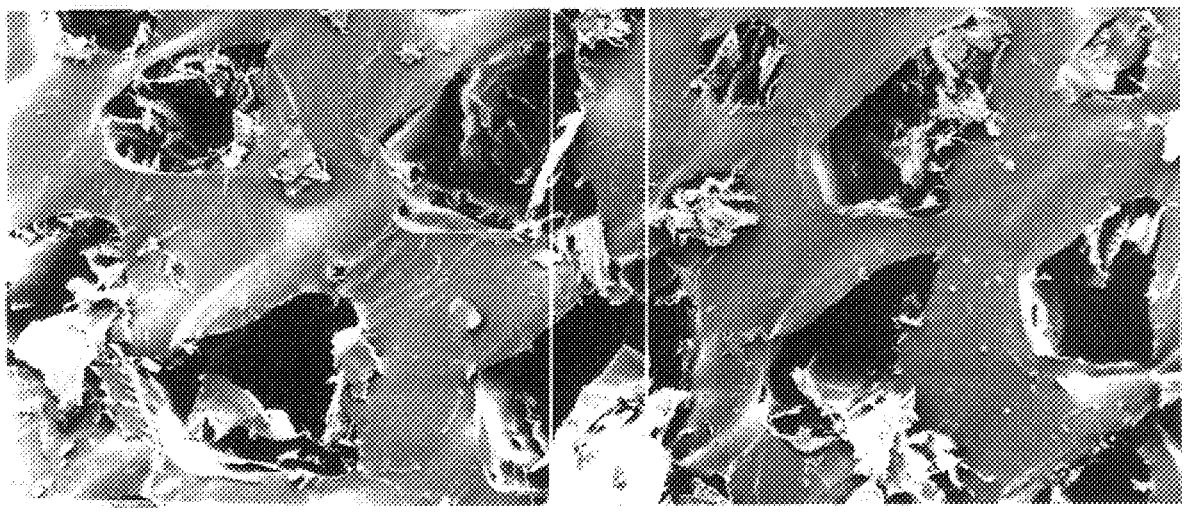
FIG. 9 is a cross-sectional view of the radial zone of cartilage region at the interface surface with alginate invested into the interstices.

A device and method according to the preferred teachings of the present invention is disclosed for treating mammalian bone and cartilage deficiencies, defects, voids and conformational discontinuities produced by congenital disformities, osseous and/or soft tissue pathology, tramatic injuries, accidental and/or surgical, and functional atrophy. The primary purpose of the anatomically specific implant device of the preferred form of the present invention is to provide the means by which chondrocytes and their attendant synthesis products, principally collagen type II, cultured in vitro, can be transported into an articular cartilage defect and be safely established therein.

Specifically, the anatomically specific device according to the preferred teachings of the present invention consists of two main parts, the cartilage region and the subchondral bone region joined at an interface surface. Each of the cartilage and the subchondral bone regions of the device includes a macrostructure composed of a bioresorbable polymer either as homogeneous polymers or combinations of two or more co-polymers from groups of, for example, poly (alpha-hydroxy acids), such as polylactic acid or polyglycolic acid or their co-polymers, polyanhydrides, polydepsipeptides, or polyorthoester. Devices fabricated for prototypes of animal studies to-date have been fabricated from the homopolymer D,D-L,L-polylactic acid.

The bioresorbable polymer in the subchondral bone region in the most preferred form is in the architecture of cancellous bone such as of the type described in U.S. Pat. Nos. 4,186,448 and 5,133,755 which are hereby incorporated herein by reference.

The cartilage region comprises 10% to 30% of the anatomically specific device and contains a tangential zone and a radial zone each having an architecturally distinct pattern. The radial zone is located intermediate or between the tangential zone and the subchondral bone region. The tangential zone is approximately 100 micrometers thick in a vertical direction and has intimate contact with the synovial fluid. Hereinafter, vertical refers to an orientation situated at right angles to the interface of the cartilage tissue with subchondral bone or in other words an orientation at right angles to the interface surface between the cartilage and subchondral bone regions of the device. This tangential zone is formed by major polymer strands which run parallel to each other and are arranged in a horizontal plane forming horizontal channels approximately 100 to 120 micrometers wide in a horizontal direction. Hereinafter, horizontal refers to an orientation situated parallel to the interface of cartilage tissue with subchondral bone or in other words an orientation parallel to the interface surface between the cartilage and subchondral bone regions of the device. The channels formed by the major polymer strands are separated from each other by a network of minor polymer strands. These minor polymer strands are also arranged in a horizontal plane, join the major polymer strands at approximately right angles, and are approximately 650 micrometers in length in a horizontal direction. All polymer strands of the tangential zone are fenestrated by multiple void spaces. The arrangement of fenestrated polymer strands produces a network of intercommunicating void spaces which have a horizontal orientation with respect to the void spaces of the radial zone.

The radial zone comprises 70% to 90% of the cartilage region. The radial zone is composed of vertically arranged, thin sheets of polymer which are fenestrated by multiple void spaces oriented in both horizontal and vertical planes. The vertically oriented void spaces of the radial zone extend, uninterrupted, from the interface surface of the cartilage and subchondral bone regions to the tangential zone. Void spaces in the horizontal plane penetrate the vertically oriented polymer sheets and create intercommunications between the vertically positioned void spaces.

The radial zone at the interface surface reveals the vertically oriented void spaces of the radial zone in cross section. The pattern of the radial zone at the interface surface formed may be described as a honeycomb pattern composed of discrete pores. The majority of discrete pores measure approximately 200 to 250 micrometers in feret diameter. These pores are generally circular. Some pores are partially occluded by a thin polymer membrane. Through these pores, there is uninterrupted void space communication from the interface surface through the radial and tangential zones to the void spaces of the tangential zone which access synovial fluid.

The architecture of the cartilage region may be formed utilizing established techniques widely practiced by those skilled in the art of bioresorbable polymers. These methods include injection molding, vacuum foaming, spinning hollow filaments, solvent evaporation, soluble particulate leaching or combinations thereof. For some methods, plasticizers may be required to reduce the glass transition temperature to low enough levels so that polymer flow will occur without decomposition.

For the devices which were fabricated for use in a rabbit's knee, the cartilage region was limited to a thickness of about 1,000 micrometers plus or minus 200 micrometers. In a human, the cartilage region can be increased to a maximum of about 3.0 mm in thickness, specifically 3,000 micrometers.

The macrostructure polymer of the cartilage region is joined or bound to the macrostructure polymer of the subchondral bone region by a process such as heat fusion which does not involve the use of solvents or chemical reactions between the two polymer segments. The resulting union between the two architectural regions is very strong and can withstand any handling required to package the device as well as any forces delivered to it as a result of the implantation technique without distorting the device's internal architecture of void spaces.

Alginate is the microstructure material most preferred in the cartilage region for the transport of in vitro and in vivo cultured cells and for the establishment of an in vivo cell culture system within a bioresorbable implant. Alginate is especially suitable for use in an anatomically specific device for treating articular cartilage defects because alginate has no known angiogenic properties and has been used successfully by others to culture and transport chondrocytes.

Alginate is a polysaccharide derived from Phaeophyceae also known as brown seawood. The most common source of alginate is the species *Macrocystis pyrifera*, the giant kelp, which grows along the coasts of North and South America, New Zealand, Australia and Africa. Other polysaccharides, such as agar and carrageenan, extracted from various types of red algae, as well as hyaluronan, also make suitable microstructure materials for bioresorbable systems designed to transport and culture chondrocytes.

Alginate is a polysaccharide polymer composed of repeating units of D-mannuronic acid, repeating units of L-guluronic acid or alternating D-mannuronic acid and L-guluronic acid residues. The exact composition of a given alginate sample depends on the subspecies of kelp (*Macrocystis pyrifera*) from which it was derived.

The most preferred form of the present invention employs a refined sodium alginate called Keltone-HV. Another preferred embodiment of the microstructure material is calcium cross-linked alginate or any other alginic acid preparation which provides a hydrocolloid gel of alginic acid suitable for the cell transport and culturing tissue at hand.

In former constructs such as U.S. Pat. No. 5,133,755, the preferred microstructure was hyaluronan which is synonymous with hyaluronic acid, hyaluronate, HA and HY. The hyaluronan was distributed uniformly throughout the internal void volume of the device. According to the teachings of the present invention, an option is provided of selecting whether or not the microstructure should be dispersed throughout all the void spaces depending on whether the arrangement is beneficial to the tissues being treated. The present invention permits incomplete dispersal as desired or complete dispersal throughout the entire void volume of the device but expressing concentration gradients of microstructure material as a means of controlling transplanted cell population numbers within the device's internal domains.

The microstructure approach can carry biologic modifiers with 1) the biodegradable polymeric macrostructure, 2) the microstructure protein, or 3) the microstructure polysaccharide.

This multiple-carrying capacity provides for five different types of locations within the device for loading biologic modifiers: 1) joined at the polymeric macrostructure interior surface; 2) joined to the chemotactic ground substance at the microstructure's exterior surface; 3) located between the biodegradable polymer and the chemotactic ground substance; 4) carried within the chemotactic ground substance in the microstructure interior; and 5) entrapped within the hydration domains of the hyaluronic acid or alginic acid microstructure yet detached from the hyaluronan/alginate polysaccharide.

At the fifth location, the biologic modifier(s) are captured by the hydration domains of the polysaccharide microstructure while the biologic modifiers are still dissolved in their original water solution. The biologically active agent(s) is attached to the hyaluronic acid or alginic acid microstructure but is not in physical contact with the polysaccharide, since it is still dissolved in water which, in turn, is entrapped within the hydration domains of the hyaluronan. This method of delivering biologically active cargo to a tissue defect is impossible with the coating approach of U.S. Pat. No. 5,041,138.

A dry filamentous velour of chemotactic ground substance, specifically RGD attachment moiety of fibronectin carried by hyaluronic acid or alginic acid velour, can be established within the void spaces of the device.

Upon saturation with water, water-based cell culture media or fluid blood, the dry velour of chemotactic ground substance is dissolved into a highly viscous gel which maintains the chemotactic ground substance as a network of dissolved polysaccharide strands, still suspended within the void volume of the polymeric macrostructure.

If the cell culture media is a fluid which saturates the device and creates the gel, then those cells suspended in the culture medium will be temporarily trapped within the gel due to the gel viscosity. The degree of gel iscosity and the length of time the gel maintains significantly high viscosities are determined by: 1) the initial molecular weight of the microstructure; 2) the microstructure in vivo rate of degradation; 3) the availability of interstitial fluid to dilute remaining microstructure and remove microstructure degradation products from the region; and 4) the initial concentration of microstructure originally placed within the macrostructure(s) interstices.

Temporarily restraining transported parenchymal cells by means of microstructure gel gives the cells time to execute two critical biologic processes. The first biologic process is the union with the microstructure via direct interaction between the microstructure and the plasma membrane CD44H receptor of the cells as well as union with the RGD attachment moiety of fibronectin which may be incorporated with the microstructure. The second biological process involves bonding with any other biologic modifiers which may be also incorporated with the microstructure or dissolved in water trapped by hydration domains of microstructure polysaccharide.

After approximately 12-to-72 hours in vivo, the microstructure gel has been reduced in viscosity to such an extent that its contents of the microstructure, which now has a reduced molecular weight, together with the surviving cell population attached to the microstructure directly or via RGD attachment moiety of fibronectin, are compelled to rest upon the structural surfaces supplied by the macrostructure polymer.

The volume of space once occupied by the microstructure gel is now occupied by the interstitial fluid and increased numbers of parenchymal cells generated by mitosis of the transplanted parent cells. In the articular cartilage regeneration of the most preferred form, it is desired to protect the transplanted cells from access to fluid blood and collateral circulation. Therefore, blood products will not be found in the void spaces of the cartilage region. In other tissue regeneration situations, however, it is desirable to attract fluid blood into the device's interstices as quickly as possible. In these situations, therefore, fibrin (i.e. blood clot), endothelial budding and granulation tissue advancing within the device interstices from sources of viable collateral circulation will be substances found within the internal void spaces of the device along with the other materials noted above.

The device interaction with cell receptors is an important advantage to the microstructure approach for achieving cell transfer. The biologic processes of cell transfer involved in U.S. Pat. No. 5,133,755 are all mediated by the interaction of various proteins and polysaccharides with specific receptors located in the plasma membrane or "cell wall" of subject cells. These specific receptors are also composed of protein.

Transplanted cells attach to the microstructure and to the RGD attachment moiety of fibronectin supported by the microstructure via interactions of the transplanted cell specific protein receptors located in their cell plasma membranes with the specific amino acid sequences or amine groups of the microstructure complex. For example, there are interactions between the transported cell receptors and the RGD attachment moiety. Another example is the direct interaction of a transported cell membrane receptor such as CD44H and hyaluronan microstructure. Still another example is the interaction of the transported cell membrane receptor and alginate microstructure.

By directly attaching transplanted cells to the three-dimensional microstructure immediately after the cells have been exposed to the transport device, the following results are obtained until the microstructure's viscosity is reduced below a critical level: 1) preserves the three-dimensional configuration of the cell; 2) preserves the entire surface area of each cell in optimum condition for interaction with the microstructure and its cargo of biologically active agents; 3) coats each cell with microstructure material which, in the case of hyaluronan, composes a high percentage of naturally occurring extracellular matrix; 4) maintains the cells, free, in a semi-fluid environment so that they can move in order to establish multiple regions of optimum cell density; 5) maintains the cells in a close proximity to high concentrations of free, solubilized and unattached biologically active agents; and 6) maintains the cargo of biologically active, therapeutic proteins carried in the hydration domains of the microstructure polysaccharide with their three-dimensional configurations undisturbed, thus optimizing their biologic activities.

In cell transplantation, the use of only a chemotactic ground substance coated on a polymeric structure can help many transplanted cells survive. However, as a result of being attached to the unyielding macrostructure surfaces, transplanted cells so attached may have distorted three-dimensional configurations and their plasma membranes may have a reduced surface area available for interaction with biologically active agents.

The present invention departs from prior practice by strategically positioning the microstructure material in that specific portion of the device which performs particular functions unique to the mature anatomy being regenerated in that vicinity. Such segregation of microstructure material within the device is based on the need to endow one portion of the device with special biologic functions that must be isolated from the remainder of the implanted device.

In a more preferred embodiment of the present invention, the microstructure has a primary purpose to deliver chondrocytes only to the cartilage region of the device and support their life function in the mammal's cartilage defect by sequestering the chondrocyte cell population together with the in vitro cell culture medium within its alginate gel. The microstructure has a secondary purpose to present enough chondrocytes to the subchondral bone region immediately adjacent to the cartilage region to insure that a competent osteo-chondral bond is established between the newly developed cartilage and the newly developed bone.

Within the inventive concept of the present invention is the establishment of variations in the concentration of microstructure within the void space network of the macrostructure in order to assure that the therapeutic elements brought from in vitro culture are present within the final device in greatest quantity where they are most needed. Examples of biologically active agents, also known as therapeutic elements and brought in from in vitro culture are cell populations, growth factors, morphogens, other therapeutic agents, drugs, etc. Such variations in concentration can be accomplished by varying concentrations of microstructure solutions prior to investment into macrostructure voids of the device or regions thereof before joining.

In the more preferred embodiment of the present invention, the alginate velour is present in highest concentration within the tangential zone of the cartilage region and the immediately adjacent locales of the radial zone. The concentration of alginate microstructure declines from the point of highest concentration toward the interface of the radial zone with the subchondral bone region. Microstructure alginate velour is present in the least concentration in the 500 to 800 micrometer thick space of the subchondral bone region.

Within the inventive concept of the present invention is the placing of two or more microstructure materials at strategic locations within the same bioresorbable implant to perform multiple and varied biologic functions segregated to specific anatomic locales of the implant device. For example, a large osteochondral defect would require hyaluronan velour for microstructure in the subchondral region intended for osteoneogenesis. In contrast, alginate velour would be more appropriate microstructure material for the cartilage region of the device intended for chondroneogenesis. The placement of different microstructure material can be accomplished by investing the microstructure material into the regions before they are joined, by investing the device or regions thereof before joining from a first surface with a desired volume of microstructure material less than the total void volume of the macrostructure and then investing from the opposite surface with a volume of a different microstructure material equal to the balance of void volume of the macrostructure.

Except for the critical location at the interface between the cartilage region, the polymer of the subchondral bone region is hydrophilic by virtue of being treated with a wetting agent such as set forth in U.S. Pat. No. 4,186,448. Beginning at about 500 to 800 micrometers from the interface surface and extending to the interface surface, the macrostructure polymer of the subchondral bone region has been rendered hydrophobic such as by treating the entire device or the subchondral bone region with a surfactant and then inactivating the surfactant on the hydrophobic barrier surfaces or by not treating the barrier surfaces with a surfactant while the remaining portions are treated. Likewise, a hydrophobic barrier may be created within a device of simple (i.e. single) or complex (i.e. multiple) internal architectures by means other than selective treatment of certain polymer regions with a surfactant. For example, a separate fibrillar construct of bioresorbable polymer may be fabricated devoid of surfactant and may be interspersed between two segments of a device whose polymers have been rendered hydrophilic.

Water-based fluids, specifically fluid blood, brought to this locale by capillary action through hydrophilic polymer of the subchondral bone region closest to subchondral bone, are prohibited from traveling further toward the cartilage region by the hydrophobic polymer of the subchondral bone region in this vicinity. The interstices of the hydrophobic fibrillar membrane would eventually accommodate cell growth, but the immediate effect of such a membrane would be to prevent passage of water-based fluids across its boundaries.

The hydrophobic barrier is a significant advance and development of devices intended for use in chondroneogenesis because hyaline cartilage, specifically the articular cartilage of joints, is an avascular tissue and must be protected from intimate contact with sources of high oxygen tension such as blood. When the recipient cartilage tissue defect is prepared to receive the implant, it is necessary to continue the defect into the underlying subchondral bone, called the cancellous bone, to assure that there will be a new bone formed beneath the cartilage region which will produce a competent bond with the newly developing cartilage.

Such tissue preparation engages the rich collateral circulation of subchondral cancellous bone and its associated bone marrow. If the cultured chondrocytes and specifically the cartilage cells come into contact with the fluid blood produced by this source of collateral circulation, they will fail to maintain their chondrocyte phenotype.

It is essential that the majority of cultured chondrocytes be protected from intimate contact with collateral circulation so that they will retain their chondrocyte phenotype and continue to produce collagen Type II in the architectural pattern dictated by the macrostructure polymer of the cartilage region. The hydrophobic barrier of the preferred form of the present invention described above achieves this objective.

It can then be appreciated that the anatomically specific bioresorbable device according to the teachings of the present invention has a fabricated macrostructure closely resembling the mature tissues which are to be regenerated by the completed implant. Further, the anatomically specific bioresorbable device of the present invention integrates the macrostructure, microstructure, cells cultured in vitro, culture medium and associated growth factors, morphogens, drugs and other therapeutic agents.

According to the preferred teachings of the present invention, the anatomically specific bioresorbable device according to the preferred teachings of the present invention can be utilized as a transport system for chondrocytes, growth factors, morphogens and other biologically active agents, in treatment of articular cartilage defects. In particular and in the preferred form, suitable source tissue is harvested and the cells are cultured using standard chondrocyte culturing methods, with the specific cell type in the most preferred form being articular cartilage chondrocyte. The cartilage defect is surgically prepared by removing diseased or damaged cartilage to create a cartilage and subchondral bone defect, with the defect extending approximately 0.5 cm to 1.0 cm into subchondral cancellous bone. With the device and defect having generally the same shape, the device is inserted into the tissue defect such as by press fitting. A volume of in vitro cell culture suspension is measured out by a microliter syringe which generally matches exactly the void volume of the cartilage region macrostructure invested by the microstructure and is injected onto the outer surface of the tangential zone of the cartilage region and which will ultimately be in contact with synovial fluid. The joint anatomy can then be replaced in proper position and the wound can be closed.

Although the preferred form relates to the transport and in vivo culturing of chondrocytes, it should be noted that the teachings of the present invention, and the useful devices fabricated as a result thereof, are intended to transport, and sustain in life, any cell type having therapeutic value to animals and plants. Examples of other cells of therapeutic value other than chondrocytes are: islets of Langerhans which produce insulin, liver parenchymal cells which have the capacity to regenerate liver tissue, and tumor cells used to stimulate the immune system against a certain tumor type.

A functionally specific device and method according to the preferred teachings of the present invention are further disclosed for facilitating healing of voids in tissue by which cellular penetration can be delayed, limited or prevented while simultaneously controlling and directing cellular growth within the interstices of the device, promoting cell attachment to structural elements of the device and allowing turnover of interstitial fluid carrying nutrients to, and waste products from, the cells, whether they are confined within the device or are external to it. These characteristics are useful to heal tissues which are in intimate contact with another tissue, wherein this intimate contact must be delayed, limited or prevented while cellular growth is occurring such as in a variety of medical applications including, but not limited to, artificial burn grafts or dressings, decubitus ulcer dressings, orbital floor implants, cleft pallet dressings, oral antral communication dressings, cranial defect dressings, controls of internal hemorrhage, vein and artery repair devices, artificial organ matrixes for regeneration of liver, kidney and pancreas, organ repair matrixes, muscle repair matrixes, bone and cartilage regeneration, delivery of drugs and other biologic modifiers, and periodontal barriers and membranes. Essentially the device of the present invention will be valuable for any healing tissue which is in intimate contact with another tissue wherein this intimate contact must be delayed, limited or prevented while cellular growth is occurring, and turnover of interstitial fluid carrying nutrients to, and waste products away from the cells both confined within and external to the device is required. Additionally, the device of the present invention may be located external to the tissue being repaired to prevent undamaged tissue from interfering with the healing tissue. The above medical applications will be obvious to those skilled in the art with the following descriptions of embodiments according to the preferred teachings of the present invention.

The biological cell trap embodiments described herein may appear complex and varied, but can all be quickly brought into focus with the analogy of an architectural interrelationship of numerous straws. Each straw forms an elongated chamber having a diameter and a length no less than two times the diameter. The elongated chambers can be randomly placed in the structure by the analogy of dumping a plurality of straws into a box creating a tangle of elongated chambers or can be organized into very elaborate designs such as being layered. The elongated chambers can be of different diameters and lengths including lengths which run the entire thickness, length, and/or width of the structure. The elongated chambers can be straight or curved. Other shaped chambers which are not elongated such as cubes, spheres, cones, irregulars, etc. may be intermixed at various concentrations with the elongated channels.

The presence of elongated chambers or channels in the internal three-dimensional architecture of the structure of the device of the present invention provides three functions. The first is structural support; the cylindrical shape being one of the strongest known in engineering. The second function provides a network or conduit system accessing the entire device through which nutrients can be introduced and waste products removed. Finally the elongated chambers provide large flattened surface areas for cell attachment.

The original use of elongated chambers or channels within the device of the present invention traps cells and controls their growth by a unique method. Central to the function of the device is the fact that cells in contact with large flat surface areas of biologically acceptable materials quickly attach and deposit an extracellular matrix. This cellular activity rapidly occludes passages through the device effectively trapping cells within the device and preventing other cells from entering the device. The combination of the bioresorbable device and attached cells creates a living tissue barrier. Over the lifetime of the device, all of the chambers will be filled, creating a tissue mass resembling the shape of the device implanted.

The properties of the device of the present invention can be enhanced or modified through simple manipulations of the architecture and the addition of additives. The architecture of the device of the present invention may be formed utilizing methods of injection molding, vacuum foaming, spinning hollow filaments, solvent evaporation, or a combination thereof.

Modifications to structure: The creation of a device where the elongated chambers are intersected by other elongated chambers will create sudden directional changes within the device which can be used to control the development of more aggressive growing tissues such as fibrous connective tissue. Further control can be achieved by layering or increasing the thickness of the device. Addition of other chambers, at various concentrations, which are not elongated provides increased control over the growth of cells and tissues.

Modifications to the surface: Modifications of the device such as partitions which partially or completely seal a surface of the device can be used to limit or prevent access to collateral circulation as well as control the location and numbers of cells which have access to the central domains of the device. Meshes or weaves can be used for size exclusion of cells or to create more surface area for platelet fracture before entrance to the device.

Controlled use of a surfactant: Addition of physiologically acceptable surfactants to porous hydrophobic bioresorbable polymers facilitates complete saturation by body fluids. Examples of surfactants include ananionic, cationic, amphoteric and nonionic surfactants. Triethanolamine dodecylbenzyl sulfonate in a concentration of 1% by mass has provided excellent results for instantaneous device saturation while lesser amounts can be utilized for slower, delayed saturation and delayed cellular migration. Additionally, a device containing a layer or portion of polymer which has not been exposed to a surfactant adjacent to a layer or portion which has, can be used to further enhance the trapping ability of the invention when in contact with aggressively growing cells by creating a breathable hydrophobic barrier.

Another novel use of surfactant in a bioresorbable porous device is for providing delayed saturation of hydrophobic layers. Increasing the amount or concentration of surfactant in the hydrophilic layers or portions so that a sufficient concentration can be liberated by interstitial fluid facilitates penetration of the fluid into the hydrophobic layer. The depth of penetration is dependent on the mass of the hydrophobic layer as it relates to the concentration of surfactant within the hydrophilic layer and availability of interstitial fluid. Specifically, a porous D,D-L,L-polylactic acid device with a layer or portion of mass containing 1.5% triethanolamine dodecylbenzyl sulfonate exposed to fetal bovine serum will draw the fetal bovine serum into the device to liberate a sufficient quantity of surfactant to facilitate incorporation or penetration of the fetal bovine serum into a layer or portion of mass which has not been exposed to or contain triethanolamine dodecylbenzyl sulfonate within 5 minutes when the flow of fluid is directed towards the hydrophobic layer.

This time may be increased or decreased by several methods including, but not limited to, having a quantity of surfactant within the hydrophobic layer which is just insufficient to impart hydrophilicity, increasing or decreasing the quantity of surfactant in the hydrophilic layer, coating of the surfactant on the polymer surface allowing it to be liberated in a shorter period of time, or any combination of the above. Thus, the device of the present invention may use a permanent, temporary, or size reducing hydrophobic barrier based on surfactant liberation.

Controlled use of a plasticizer: When required, plasticizers, in a mass not to exceed 50% of the mass of the entire device, can be incorporated into the device to provide flexibility. This addition may be necessary when the bioresorbable polymer utilized does not provide sufficient flexibility to the device or the molecular weight of the material is so low as to result in a brittle device.

An additional novel use of a plasticizer in a porous bioresorbable polymer is for temporary flexibility. A plasticizer such as triethyl citrate, which is extractable in body fluids, is used to conform the device, during implantation into the tissue to be healed and regenerated. The plasticizer is leached out of the device leaving it less flexible and relatively rigid. Other citric acid esters are water extractable, specifically those with molecular weights less than 402 daltons.

Other additives: Biologically active agents such as physiologically acceptable drugs, biological modifiers, proteins, hormones, and antigens and mixtures thereof may also be utilized with the device of the present invention by either incorporating the additives within the bioresorbable mass or attaching them to the surfaces of the bioresorbable mass. These substances may be used to enhance the primary purpose of the device or may use the device of the present invention to achieve a secondary purpose.

It can be realized that like the surfactant, the plasticizers and/or other additives can be included in portions of the device while other portions of the device of the present invention can be substantially free of the lasticizer and/or other additives.

PREFERRED BIOLOGICAL CELL TRAP EMBODIMENT OF THE INVENTION

Figure 10:
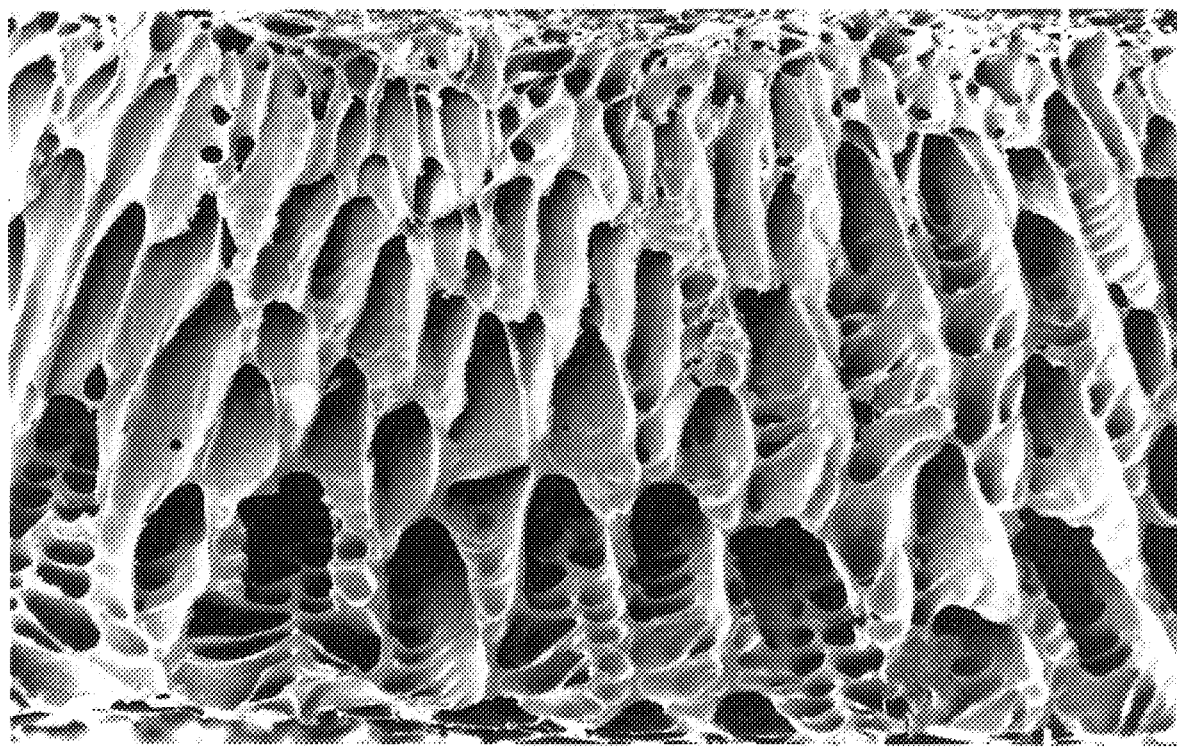
FIG. 10 is a cross-sectional view of a periodontal barrier according to the preferred teachings of the present invention.
Figure 11:
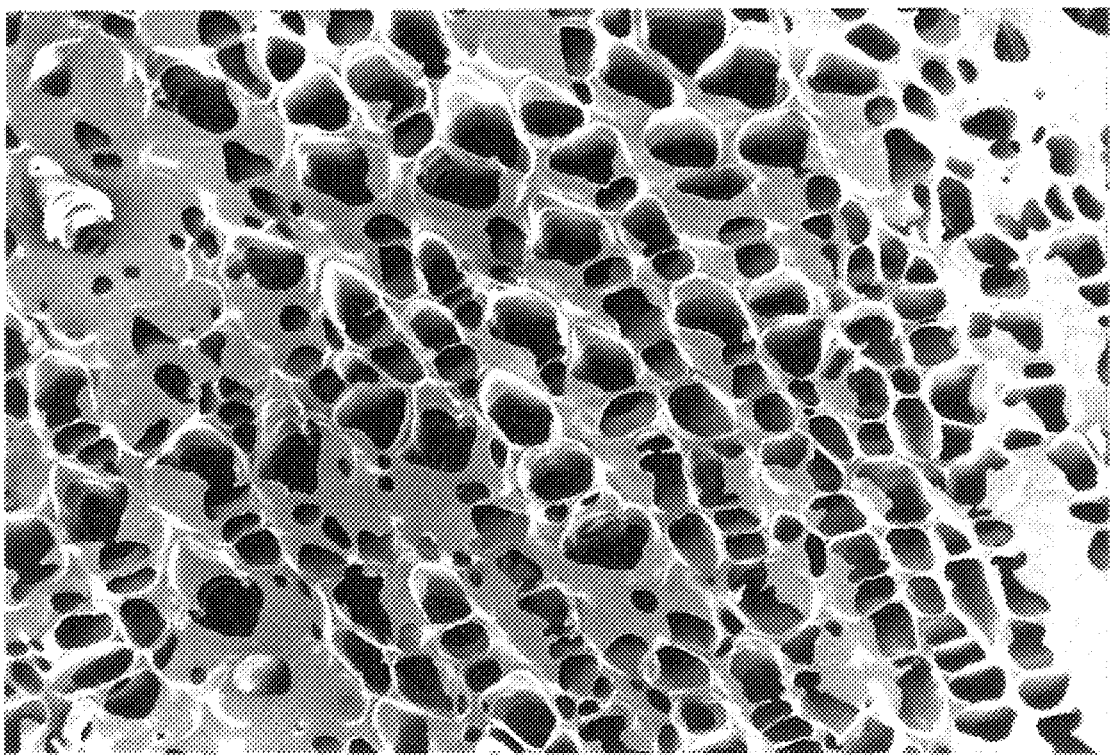
FIG. 11 is a view of the surface of the periodontal barrier of FIG. 10 which interfaces with the mucoperiosteum.
Figure 12:
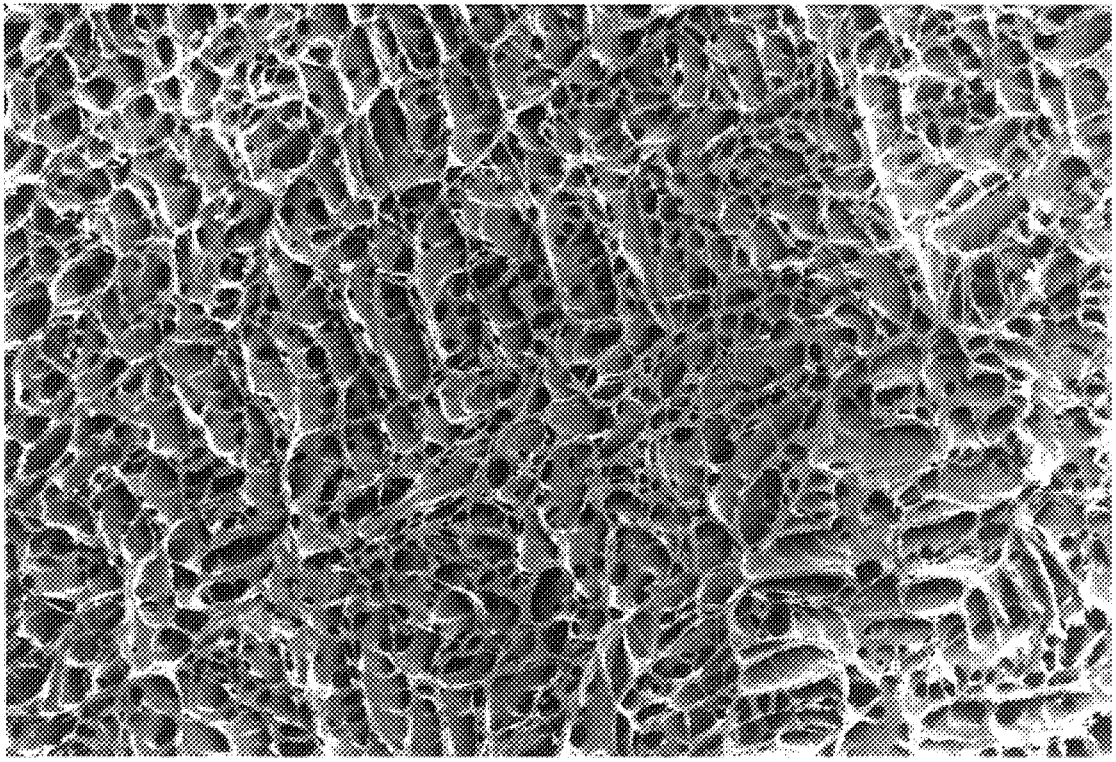
FIG. 12 is a view of the surface of the periodontal barrier of FIG. 10 which interfaces with the bone void.

The preferred embodiment of the invention is in the form of a device for use as a periodontal barrier utilized in restorative surgeries. In particular, the device is formed of a biocompatible material including bioerodable materials and polymer materials and bioresorbable materials and polymer materials such as a polymerized alpha-hydroxy acid. In the most preferred form, D,D-L,L-polylactic acid is fabricated, in the presence of 0.5% triethanolamine dodecylbenzyl sulfonate by mass, into sheets ranging from 350 to 500 microns in thickness. As best seen in FIG. 10, the body of the device is composed of multiple elongated chambers which are intersected by other elongated chambers resulting in sudden directional changes which delay penetration of aggressive growing fibroblasts until sufficient quantities of new bone have formed to fill the deficiency. The surface of the device at the interface with the mucoperiosteum as best seen in FIG. 11 is composed of a tightly woven mesh of D,L-polylactic acid. The surface of the device in contact with the bone void as best seen in FIG. 12 has 20–35% of the elongated chambers sealed off with solid partitions. This device, when placed over baboon periodontal defects and contacting the tissue to be healed and regenerated, is invaded by fibroblasts at a rate of 20% per month delaying contact with the healing bone void for 5 months.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

We claim:

1. Functionally specific device for facilitating healing of voids in tissue comprising a structure made from a biocompatible material providing an internal three-dimensional architecture comprising a plurality of elongated chambers, with each of the elongated chambers having a diameter and a length, with the length being no less than two times the diameter of the chamber, with the chambers being sized such that desired cellular activity rapidly occludes the chambers effectively trapping the desired cells within the chambers and initially preventing other cells from entering the chambers.

2. The device of claim 1 wherein the structure has a thickness, with the elongated chambers running the entire thickness of the structure.

3. The device of claim 1 wherein the structure has a length and a width, with the elongated chambers running the entire length and width of the structure.

4. The device of claim 1 wherein the enlongated chambers are layered within the structure.

5. The device of claim 1 wherein the elongated chambers are randomly placed within the structure.

6. The device of claim 1 further comprising, in combination: additional chambers which are not elongated and are intermixed with the elongated chambers.

7. The device of claim 1 wherein the structure includes at least one surface which is completely sealed by partitions.

8. The device of claim 6 wherein the structure includes at least one surface covered by a mesh formed of bioerodable/bioresorbable material.

9. The device of claim 1 wherein at least a portion of the structure includes a physiologically acceptable surfactant selected from the group consisting of ananionic, cationic, amphoteric and nonionic surfactants.

10. The device of claim 9 wherein the surfactant is triethanolomine dodecylbenzyl sulfonate.

11. The device of claim 1 wherein at least a first portion of the structure has incorporated a fluid extractable plasticizer providing temporary flexibility during implantation.

12. The device of claim 11 wherein the plasticizer is contained in the structure in an amount not to exceed 50% by weight of the entire structure.

13. The device of claim 11 wherein the plasticizer is triethyl citrate.

14. The device of claim 1 wherein at least a first portion of the structure includes a biologically active agent.

15. The device of claim 14 wherein the biologically active agent is selected from the group consisting of a physiologically acceptable drug, a biological modifier, a protein, a hormone, and antigen and mixtures thereof.

16. The device of claim 1 wherein the biocompatible material is a material selected from the group consisting of bioerodable materials, bioresorbable materials, bioerodable polymer materials, and bioresorbable polymer materials.

17. The device of claim 16 wherein the biocompatible material is a polymerized alpha-hydroxy acid.

18. The device of claim 17 wherein the polymerized alpha-hydroxy acid is D,L-polylactic acid.

19. The device of claim 1 wherein at least some of the elongated chambers communicate with other chambers.

20. The device of claim 1 wherein at least some of the elongated chambers intersect with other chambers.

21. The device of claim 1 wherein the structure includes at least one surface which is partially sealed by partitions.

22. A method of healing and tissue regeneration comprising contacting the tissue to be healed and regenerated with the device defined in claim 1.

23. A method as defined in claim 22 wherein the device is implanted into the tissue to be healed and regenerated.

24. A method as defined in claim 23 wherein the device allows tissue integration of the device while delaying total penetration through the device by tissue cells, thereby providing space maintenance and regeneration of tissue external to the device and controlled growth of tissue forming cells within the device.

25. Functionally specific device for facilitating healing of voids in tissue comprising a structure made from a biocompatible material providing an internal three-dimensional architecture comprising a plurality of elongated chambers, with each of the elongated chambers having a diameter and a length, with the length being no less than two times the diameter of the chamber; wherein at least a portion of the structure includes a physiologically acceptable surfactant in an amount sufficient to draw fluid into the structure to liberate a quantity of surfactant sufficient to facilitate penetration of the fluid into a portion of the structure not containing surfactant.

26. Functionally specific device for facilitating healing of voids in tissue comprising a structure made from a biocompatible material providing an internal three-dimensional architecture comprising a plurality of elongated chambers, with each of the elongated chambers having a diameter and a length, with the length being no less than two times the diameter of the chamber; wherein the structure includes a first portion having incorporated a fluid extractable plasticizer providing temporary flexibility during implantation and includes a second portion which is substantially free of the plasticizer.

27. Functionally specific device for facilitating healing of voids in tissue comprising a structure made from a biocompatible material providing an internal three-dimensional architecture comprising a plurality of elongated chambers, with each of the elongated chambers having a diameter and a length, with the length being no less than two times the diameter of the chamber; wherein the structure includes a first portion having a biologically active agent and includes a second portion which is substantially free of the biologically active agent.

28. A method of healing and tissue regeneration comprising contacting the tissue to be healed and regenerated with a functionally specific device for facilitating healing of voids in tissue comprising a structure made from a biocompatible material providing an internal three-dimensional architecture comprising a plurality of elongated chambers, with each of the elongated chambers having a diameter and a length, with the length being no less than two times the diameter of the chamber; wherein the device is disposed externally to the tissue sought to be repaired to prevent undamaged tissue from interfering with the tissue sought to be repaired.

29. Bioresorbable device comprising, in combination: first and second portions; and a physiologically acceptable surfactant engaged with the first portion and the second portion being initially substantially free of the surfactant, with the initial concentration of the surfactant in the first portion being effective to preclude surfactant from being drawn into the second portion, with the initial concentration of the surfactant in the first portion being effective to permit surfactant to be drawn into the second portion when fluid is eventually drawn into the first portion such that the fluid is eventually drawn into the second portion.

30. The device of claim 29 wherein the initial concentration of the surfactant in the first portion is effective to permit surfactant to be drawn into the second portion when serum is eventually drawn into the first portion.

31. Bioresorbable device for implantation into a body having body fluids comprising, in combination: a structure made from a biocompatible material; and a fluid extractable plasticizer incorporated in the structure, with the plasticizer permitting the structure to be initially flexible during implantation, with the plasticizer being extractable from the structure by the body fluids after implantation whereby the structure is rendered less flexible.

* * * * *